(12) United States Patent
Wu et al.

(10) Patent No.: US 6,543,275 B2
(45) Date of Patent: Apr. 8, 2003

(54) APPARATUS AND METHOD FOR TESTING AIR PERMEABILITY OF A FABRIC

(75) Inventors: Richard Wu, Hsinchu (TW); Shih-Jen Chang, Hsin-Chu (TW)

(73) Assignee: Taiwan Semiconductor Manufacturing Co., Ltd, Hsin Chu (TW)

( * ) Notice: Subject to any disclaimer, the term of this patent is extended or adjusted under 35 U.S.C. 154(b) by 20 days.

(21) Appl. No.: 09/898,433

(22) Filed: Jul. 2, 2001

(65) Prior Publication Data

US 2003/0000287 A1 Jan. 2, 2003

(51) Int. Cl.[7] ................................................ G01M 3/00
(52) U.S. Cl. ............................................... 73/38; 73/159
(58) Field of Search ...................................... 73/38, 159

(56) References Cited

U.S. PATENT DOCUMENTS

| | | | | |
|---|---|---|---|---|
| 1,827,562 A | * | 10/1931 | Carpertner ..................... 73/38 |
| 4,779,448 A | * | 10/1988 | Gogins ........................... 73/38 |
| 5,858,791 A | * | 1/1999 | Lemaire ......................... 73/38 |
| 5,887,477 A | * | 3/1999 | Newman ....................... 73/159 |
| 6,196,055 B1 | * | 3/2001 | Haines ........................... 73/38 |
| 6,324,898 B1 | * | 12/2001 | Cote et al. ..................... 73/38 |
| 6,422,063 B1 | * | 7/2002 | Anantheswaran et al. ..... 73/38 |

* cited by examiner

*Primary Examiner*—Daniel S. Larkin
*Assistant Examiner*—Michael Cygan
(74) *Attorney, Agent, or Firm*—Tung & Associates

(57) ABSTRACT

An apparatus and a method for testing permeability of a clean room garment material are described. The apparatus is constructed by a flow regulator, a flow meter, a sample holder and a quantitative tube that is equipped with a fluid reservoir for generating a bubble through the tube. The components of the apparatus can be readily obtained and the apparatus can be constructed at low cost. The method for testing air permeability can be conducted easily by utilizing the present invention novel apparatus in a factory environment without elaborate and expensive equipment.

18 Claims, 1 Drawing Sheet

APPARATUS AND METHOD FOR TESTING AIR PERMEABILITY OF A FABRIC

FIELD OF THE INVENTION

The present invention generally relates to an apparatus and a method for testing the property of a fabric and more particularly, relates to an apparatus and a method for testing the air permeability of a fabric by using a quantitative tube filled with a soap solution.

BACKGROUND OF THE INVENTION

In the recent development of semiconductor fabrication technology, the continuous miniaturization device fabricated demands more astringent requirements in the fabrication environment and contamination control. When the feature size was in the 2 μm range a cleanliness class of 100~1,000 (i.e., the number of particles at sizes larger than 0.5 μm per cubic foot) was sufficient. However, when the feature size is reduces 0.25 μm, a cleanliness class of 0.1 becomes necessary.

It has been proposed that an inert mini-environment may be the solution to future fabrication technologies when the device size is further reduced. In order to eliminate micro-contamination and to reduce native oxide growth on silicon surfaces, the wafer processing and the loading/unloading procedures of a process tool must be enclosed in a extremely high cleanliness mini-environment that is constantly flushed with ultra pure nitrogen that no oxygen or moisture.

Different approaches in modern clean room design has been pursued in recent years in the advent of the ULSI technology. One is the utilization of a tunnel concept in which a corridor separates the process area from the service area in order to achieve a high level of air cleanliness. Under the concept, the majority of equipment maintenance functions are conducted in low-classified service areas, while the wafers are handled and processed in more costly high-classified tunnels. For instance, in a process for 16 M and 64 M DRAM products, the requirements of contamination control in a process environment is so stringent that the control of the enclosure of the process environment for each process tool must be considered. In order to maintain the high cleanliness class required, the loading and unloading of the process tool must handled automatically by an input/output device such as a SMIF apparatus. The clothing of the machine operator must also be stringently cleaned without introducing particle contaminations into the clean room.

The continuous monitoring of particles, temperature and humidity conditions inside a clean room is required for alerting engineers to changes occurring in the clean room environment such that steps may be taken to prevent particle-sensitive fabrication processes from drifting out of control. The proper gowning procedure and clean room maintenance practices are both critical to prevent any possible micro-contamination in the clean room.

It has long been recognized that the human operators are major sources of clean room contaminants. For instance, not only the operators generate a large number of contaminants, the operators are also in close proximity to the wafers at many different stages of the fabrication process. As a result, a proper gowning procedure becomes critical in minimizing the exposure of human hair, bare skin and contaminants carried on street clothes.

To minimize human contamination, it has been a practice in IC fabrication facilities to require its clean room operators to change from street clothes and street shoes into company-provided clean room suit, a face mask and booties over the street shoes. These clean room suits, masks and booties are worn on the outside of street clothes of clean room operators in a designated area immediately adjacent to a clean room normally known as a gowning room.

A good clean room suit material is normally made of woven fabrics that consist of long synthetic fibers covered with a layer of low friction polymeric material. The polymeric coating material prevents particles from passing through while at the same time allows vapor transmission. The clean room suits and booties are washed regularly using deionized water and sodium-free detergent. Stringent procedures must be followed in providing laundry services to the suits and booties in order to minimize contamination while washing, packaging, transporting, and storing these clean room garments.

A good clean room suit material also requires good breathability or air permeability such that the suit can be worn comfortably by a clean room operator. While the air permeability quality is important, it must be balanced by the possible emission of particles from the human body. For instance, the air permeability must not be so high that the particle counts from a human body increases. The air permeability property of a clean room suit material must therefore be limited by the particle emission property and thus, must be controlled within a suitable range.

Traditionally, the air permeability property of a fabric material is tested by a differential pressure technique in which the pressure difference in two chambers that are separated by a piece of fabric are determined. However, such determination requires specialized equipment for pressurizing the chambers and for making sensitive measurements of a pressure change. The test can not be easily conducted in a factory environment and furthermore, the test apparatus cannot be easily mobilized.

It is therefore an object of the present invention to provide an apparatus for testing the air permeability of a fabric that does not have the drawbacks or shortcomings of the conventional methods.

It is another object of the present invention to provide an apparatus for testing the air permeability of a fabric which can be easily used in a factory environment.

It is a further object of the present invention to provide an apparatus for testing the air permeability of a fabric which can be easily assembled by components that are readily available.

It is another further object of the present invention to provide an apparatus for testing the air permeability of a fabric by using a flow regulator, a flow meter, a sample holder and a quantitative tube.

It is still another object of the present invention to provide an apparatus for testing air permeability of a fabric by utilizing a quantitative tube in which a water solution of soap is utilized to generate bubbles.

It is yet another object of the present invention to provide a method for testing air permeability of a fabric by utilizing a simple arrangement of a test apparatus.

It is still another further object of the present invention to provide a method for testing air permeability of a fabric by utilizing a quantitative tube and determining the amount of time for a soap bubble to travel through the tube.

SUMMARY OF THE INVENTION

In accordance with the present invention, an apparatus and a method for testing air permeability of a fabric are provided.

In a preferred embodiment, an apparatus for testing the air permeability of a fabric can be provided which includes a flow regulator for controlling the flow rate of an air flow therethrough; a flow meter in fluid communication with the flow regulator for indicating an air flow rate; a sample holder in fluid communication with the flow meter for holding a fabric sample therein such that the air flow passes through the fabric sample exiting an outlet tube; and a quantitative tube equipped with an arch portion that is optically transparent in fluid communication with a gas outlet on top of the quantitative tube and a fluid reservoir at a bottom of the quantitative tube, the fluid reservoir for holding a quantity of a fluid that generates bubbles when air passes over a top surface of the fluid and is connected to the enlarged portion by a tube section, the tube section is further in fluid communication with the outlet tube of the sample holder for admitting the air flow flown through the fabric sample and for exiting the air flow from the gas outlet on top.

The apparatus for testing the air permeability of a fabric may further include a shut-off valve situated upstream of the flow regulator for turning on or off the air flow. The sample holder may be formed in a cylindrical tube that holds a fabric sample under a hollow cap at one end of the cylindrical tube, the sample holder may also be a cylindrical tube that is formed of a plastic material and provided with a plurality of vent holes for buffering the air flow passing through the fabric sample. The apparatus may further include plastic tubing means providing fluid communication in-between the flow regulator, the flow meter, the sample holder and the quantitative tube. The quantitative tube may be formed of glass, the flow meter may be of the gravity ball type. The sample holder may be a PVC tube that has a plurality of apertures drilled therethrough. The quantity of fluid that generates bubbles when air passes over a top surface of the fluid may be a water solution of soap. The flow regulator may be a butterfly valve. The enlarged portion of the quantitative tube is provided with a lower mark and an upper mark at two extreme ends of the enlarged portion.

The present invention is further directed to a method for testing air permeability of a fabric which can be carried out by the operating steps of first providing a flow regulator, a flow meter, a sample holder and a quantitative tube that are in fluid communication with each other, then flowing an air flow through the flow regulator, the flow meter, the sample holder and a fabric sample such that a bubble is generated from a quantity of fluid kept in the quantitative tube and observing the bubble rising up through a lower mark and an upper mark in the quantitative tube; and then counting the time required for the bubble to pass from the lower mark to the upper mark as an indication of the air permeability of the fabric sample.

In the method for testing air permeability of a fabric, the sample holder may be a PVC tube that has a plurality of ventilation holes therethrough, the sample holder may be a cylindrical tube that has a diameter of about 1 cm, the enlarged portion of the quantitative tube may have a volume of about 90 cm$^3$ between the lower mark and the upper mark such that a relative air permeability can be calculated by an equation of 90/(number of seconds for bubble to rise) (cross-sectional area of sample tube). The method may further include the step of providing a shut-off valve that is situated upstream of the flow regulator for turning on or off the air flow. The method may further include the step of buffering the air flow by the plurality of vent holes provided through the sample holder tube. The method may further include the step of connecting the flow regulator, the flow meter, the sample holder and the quantitative tube in fluid communication by PVC tubes, or the step of generating a bubble from the quantity of fluid prepared by dissolving soap in water.

BRIEF DESCRIPTION OF THE DRAWING

These and other objects, features and advantages of the present invention will become apparatus from the following detailed description and the appended drawings in which.

DETAILED DESCRIPTION OF THE PREFERRED EMBODIMENT

Figure 1:
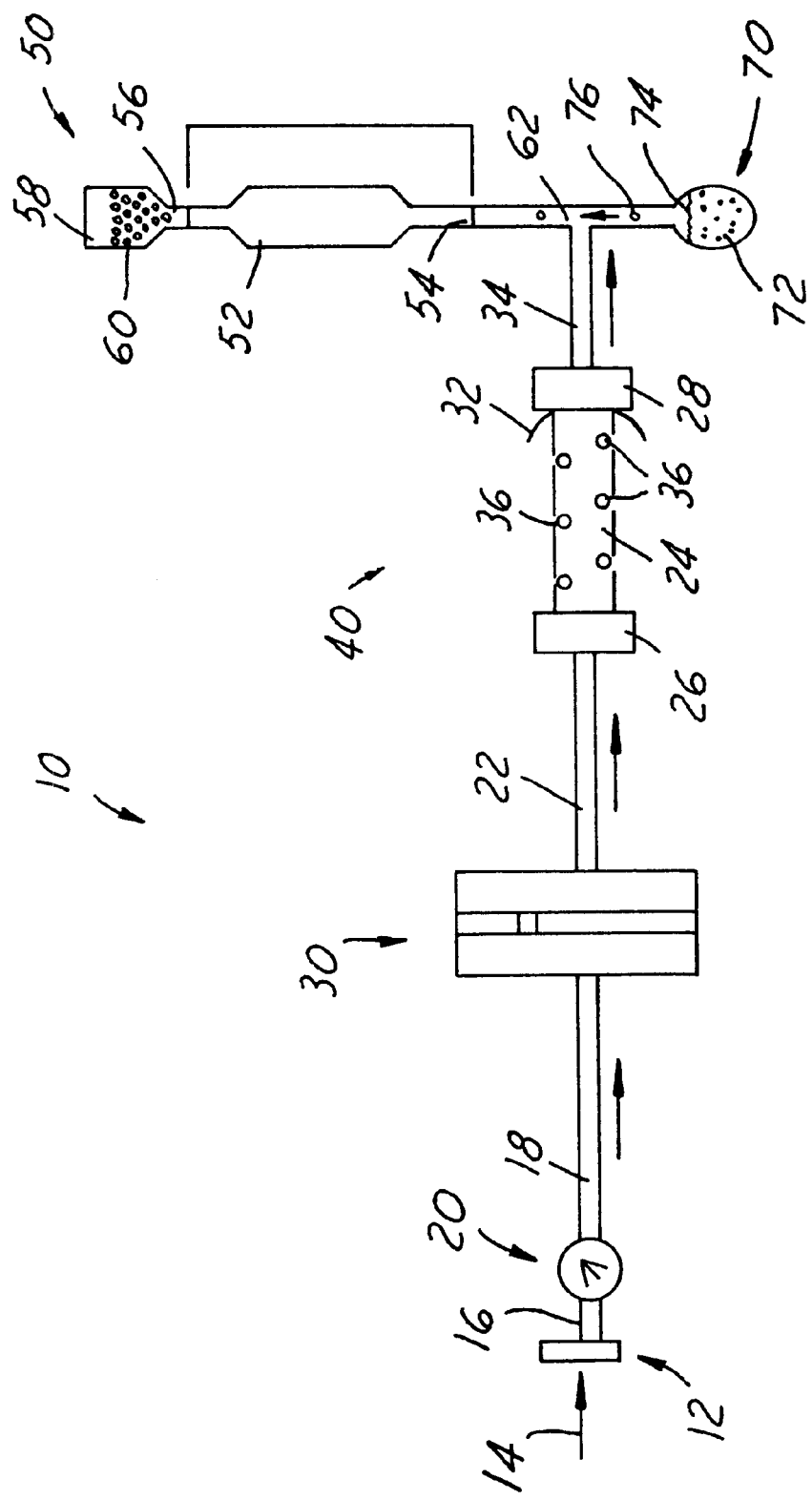
FIG. 1 is a schematic of the present invention apparatus for testing air permeability of a fabric.

The invention discloses an apparatus for testing the air permeability of a fabric material, the apparatus is particularly suitable for testing the air permeability of a clean room garment material. The apparatus is constructed by a flow regulator, a flow meter, a sample holder and a quantitative tube. The apparatus may further include a shut-off valve situated upstream of the flow regulator.

In the system, the flow regulator is used for controlling the flow rate of an air flow through the apparatus, while the flow meter is connected in fluid communication with the flow regulator for indicating an air flow rate. The sample holder is further in fluid communication with the flow meter for holding a fabric sample such that an air flow may pass through the fabric sample to exit an outlet tube. The quantitative tube is equipped with an enlarged portion that is optically transparent in fluid communication with a gas outlet on top of the quantitative tube and a fluid reservoir at a bottom of the quantitative tube. The fluid reservoir is used to hold a quantity of a fluid that generates bubbles when air passes over a top surface of the fluid. The fluid reservoir is connected to the enlarged portion of the quantitative tube by a tube section. The tube section is further in fluid communication with the outlet tube of the sample holder for admitting an air flow that is flown through the fabric sample and for exiting the air flow from the gas outlet on top of the quantitative tube.

The enlarged portion of the quantitative tube is provided with a lower mark and an upper mark at two extreme ends of the enlarged portion.

The invention further discloses a method for testing air permeability of a clean room garment material by using the aforementioned apparatus. The method is carried out by first flowing an air flow through the flow regulator, the flow meter, the sample holder and a fabric sample that is fastened to the sample holder such that a bubble is generated by the quantity of fluid and rising up through the lower mark and the upper mark of the quantitative tube. The amount of time required for a bubble to pass from the lower mark to the upper mark is then determined as an indication of the air permeability of the fabric material.

The present invention apparatus can be easily assembled together with components that are readily available. The components are low cost components, such that the apparatus can be assembled together at very little expense. The apparatus can be used to perform an air permeability test of a clean room garment material to evaluate the breathability or air permeability of the material.

The present invention apparatus 10 for conducting an air permeability test for a fabric material is shown in FIG. 1. The apparatus 10 is constructed by four major components of a flow regulator 20, a flow meter 30, a sample holder 40 and a quantitative tube 50. The apparatus may optionally include a shut-off valve 12 installed upstream of the flow regulator 20. The shut-off valve 12 admits an air flow or cut-off an air flow 14 into the flow regulator 20, which may be suitably a butterfly valve or any other type of flow regulators. The air flow passes through an air conduit 16, 18 into a flow meter 30, which may be suitably a gravity ball type such that the air flow rate can be easily read on a graduated scale on the side of the meter. The air flow then passes through air conduit 22 into a sample holder 40.

The sample holder 40 can be advantageously constructed by a hard plastic material, such as PVC. The sample holder 40 is constructed by a PVC tube 24 with two hollow end caps 26 and 28 fastened to the two ends of the tube. The two hollow end caps 26, 28 may be screwed onto the PVC tube 24, or may be compression fitted to the ends of the tube. The hollow end cap 26 allows an air tight connection with the air conduit 22, while the hollow end cap 28 allows an installation of a fabric sample 32 and the air tight connection to air conduit 34.

In a preferred embodiment, the sample holder tube 24 is constructed in PVC with a diameter of about 1 cm which produces a cross-sectional area of about 3 cm$^2$. As shown in FIG. 1, the PVC tube 24 is further provided, i.e., or drilled, with a plurality of ventilation holes 36 such that an air flow 14 through the sample holder 40 can be buffered and does not damage the fabric sample 32 in the event that the air flow 14 is too high. The ventilation apertures 36 may be suitably provided in a diameter between about 1 mm and about 3 mm.

After the air flow 14 passes through the fabric sample 32 clamped by the end cap 28, it passes through air conduit 34 into a quantitative tube 50.

The quantitative tube 50 is most suitably fabricated in a glass material such that the rising up of a bubble can be readily examined visually. The quantitative tube 50 is constructed with an enlarged portion 52 which is provided with a lower mark 54 and an upper mark 56 on the glass wall. The volume in the enlarged portion 52 between the two marks 54, 56 is approximately 90 cm$^3$. On top of the quantitative tube 50, is connected with a gas outlet 58 which may be filled with sintered glass beads 60 to prevent the escape of bubbles from the gas outlet 58, while allowing air to escape.

On the other extreme end of the quantitative tube 50, is connected in fluid communication with the enlarged portion 52 a fluid reservoir 70 used to hold a quantity of a fluid 72 for generating bubbles when air is passed over a top surface 74 of the quantity of fluid 72. In the present invention preferred embodiment, a water solution of a soap is suitably used as the quantity of fluid 72 such that soap bubble can be produced to rise up the connecting tube 62 in-between the fluid reservoir 70 and the enlarged portion 52 of the quantitative tube 50. The connecting tube 62 is further provided with a T-shaped connection to the air conduit 34 such that an air flow 14 that passes through the fabric sample 32 may enter into the quantitative tube 50 and carry with it a soap bubble upwardly through the quantitative tube 50.

It should be noted that any other suitable bubble-generating fluid may also be used in the present invention fluid reservoir 72 to produce bubbles. As a bubble 76 is produced by the air flow 14 through the connecting tube 62 upwardly, the bubble 76 first passes through the lower mark 54 into the enlarged portion 52, and then passes through the upper mark 56 and is trapped by the sintered glass beads 60 while air escapes through the outlet 58. Since the quantitative tube 50 is fabricated of a glass material, the generation of the bubble 76 and the traveling of bubble 76 through the enlarged portion 52 of the quantitative tube 50 can be easily observed and as a result, the total period of time needed for the bubble 76 to travel between the lower mark 54 and the upper mark 56 can be determined.

The present invention method for testing air permeability of a clean room garment material can be carried out by first flowing an air flow 14 through the flow regulator 20, the flow meter 30, the sample holder 40 and the fabric sample 32 such that a bubble 76 is generated from the quantity of fluid 72 and rises up through the lower mark 54 and the upper mark 56 of the quantitative tube 50. The time required for the bubble 76 to pass from the lower mark 54 to the upper mark 56 is thus determined and used to calculate the air permeability by the following equation:

Relative Air Permeability =90/(number of seconds of bubbles to rise from lower mark to upper mark)×(cross-sectional area of sample tube)

In the present illustrative example, the enlarged portion 52 of the quantitative tube 50 has a volume of about 90 cm$^3$ which is used in the equation. When the diameter of the sample holder 40 is about 1 cm, which gives a cross-sectional area of about 3 cm$^2$, and when the total number of seconds for the bubble to rise passing the lower mark and the upper mark is determined to be about 30 seconds, the relative air permeability determined is about 1.

After the determination of several acceptable garment material that have been used in the clean room garments, it was determined that a suitable relative air permeability is between a numerical value of 1 and 3. These numbers represent an acceptable range of the relative air permeability, while the particle count from human body is maintained at an acceptable level.

The present invention apparatus and method for testing air permeability of a clean room garment material have therefore been amply described in the above description and in the appended drawing of FIG. 1.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows:

What is claimed is:

1. An apparatus for testing the air permeability of a fabric comprising:

a flow regulator for controlling the flow rate of an air flow therethrough;

a flow meter in fluid communication with said flow regulator for indicating an air flow rate;

a sample holder in fluid communication with said flow meter for holding a fabric sample therein such that said air flow passes through the fabric sample exiting an outlet tube; and a quantitative tube equipped with an enlarged portion that is optically transparent in fluid communication with a gas outlet on top of the quantitative tube and a fluid reservoir at a bottom of the quantitative tube, said fluid reservoir for holding a quantity of a fluid that generates bubbles when air passes over a top surface of the fluid and is connected to said enlarged portion by a tube section, said tube section is further in fluid communication with said outlet tube of said sample holder for admitting said air flow flown through said fabric sample and for exiting said air flow from said gas outlet on top.

2. An apparatus for testing the air permeability of a fabric according to claim 1 further comprising a shut-off valve situated upstream of said flow regulator for turning on or off said air flow.

3. An apparatus for testing the air permeability of a fabric according to claim 1, wherein said sample holder being a cylindrical tube that holds a fabric sample under a hollow end cap at one end of the cylindrical tube.

4. An apparatus for testing the air permeability of a fabric according to claim 1, wherein said sample holder being a cylindrical tube formed of a plastic material and provided with a plurality of vent holes for buffering said air flow passing through the fabric sample.

5. An apparatus for testing the air permeability of a fabric according to claim 1 further comprising plastic tubing means providing fluid communication in-between said flow regulator, said flow meter, said sample holder and said quantitative tube.

6. An apparatus for testing the air permeability of a fabric according to claim 1, wherein said quantitative tube being formed of glass.

7. An apparatus for testing the air permeability of a fabric according to claim 1, wherein said flow meter is of the gravity ball type.

8. An apparatus for testing the air permeability of a fabric according to claim 1, wherein said sample holder being a PVC tubing having a plurality of apertures drilled therethrough.

9. An apparatus for testing the air permeability of a fabric according to claim 1, wherein said quantity of fluid that generates bubbles when air passes over a top surface of the fluid is a water solution of soap.

10. An apparatus for testing the air permeability of a fabric according to claim 1, wherein said flow regulator is a butterfly valve.

11. An apparatus for testing the air permeability of a fabric according to claim 1, wherein said enlarged portion of said quantitative tube is provided with a lower mark and an upper mark at two extreme ends of said enlarged portion.

12. A method for testing air permeability of a fabric comprising the steps of:
   providing a flow regulator for controlling the flow rate of an air flow therethrough;
   a flow meter in fluid communication with said flow regulator for indicating an air flow rate; a sample holder in fluid communication with said flow meter for holding a fabric sample therein such that said air flow passes through the fabric sample exiting an outlet tube; and a quantitative tube equipped with an enlarged portion that is optically transparent in fluid communication with a gas outlet on top of the quantitative tube and a fluid reservoir at a bottom of the quantitative tube, said fluid reservoir for holding a quantity of a fluid that generates bubbles when air passes over a top surface of the fluid and is connected to said enlarged portion by a tube section, said tube section is further in fluid communication with said outlet tube of said sample holder, said enlarged portion of the quantitative tube being provided with a lower mark and an upper mark located at two extreme ends of said enlarged portion;
   flowing an air flow through said flow regulator, said flow meter, said sample holder and said fabric sample such that a bubble is generated from said quantity of fluid and rises up through said lower and said upper mark of said quantitative tube; and
   counting the time required for said bubble to pass from said lower mark to said upper mark of said quantitative tube.

13. A method for testing air permeability of a fabric according to claim 12, wherein said sample holder is a PVC tube having a plurality of ventilation holes therethrough.

14. A method for testing air permeability of a fabric according to claim 12, wherein said sample holder is a cylindrical tube having a diameter of about 1 cm, said enlarged portion of the quantitative tube has a volume of about 90 $cm^3$ between said lower mark and said upper mark such that a relative air permeability is calculated by the equation of:

Relative Air Permeability=90/(#seconds for bubbles to rise)(cross-sectional area of sample tube).

15. A method for testing air permeability of a fabric according to claim 12 further comprising the step of providing a shut-off valve situated upstream of said flow regulator for turning on or off said air flow.

16. A method for testing air permeability of a fabric according to claim 12 further comprising the step of buffering said air flow by said plurality of vent holes provided through said sample holder tube.

17. A method for testing air permeability of a fabric according to claim 12 further comprising the step of connecting said flow regulator, said flow meter, said sample holder and said quantitative tube in fluid communication by PVC tubes.

18. A method for testing air permeability of a fabric according to claim 12 further comprising the step of generating a bubble for said quantity of fluid prepared by dissolving soap in water.

* * * * *